(12) United States Patent
Mizuno

(10) Patent No.: US 7,223,232 B2
(45) Date of Patent: May 29, 2007

(54) ENDOSCOPE PROBE SYSTEM HAVING CONFOCAL OPTICAL SYSTEMS

(75) Inventor: Rogerio Jun Mizuno, Saitama-ken (JP)

(73) Assignee: PENTAX Corporation, Tokyo (JP)

( * ) Notice: Subject to any disclaimer, the term of this patent is extended or adjusted under 35 U.S.C. 154(b) by 339 days.

(21) Appl. No.: 10/759,208

(22) Filed: Jan. 20, 2004

(65) Prior Publication Data
US 2004/0147810 A1 Jul. 29, 2004

(30) Foreign Application Priority Data
Jan. 21, 2003 (JP) ............................. 2003-012787

(51) Int. Cl.
*A61B 1/04* (2006.01)
*G02B 21/06* (2006.01)
*G01J 3/30* (2006.01)

(52) U.S. Cl. ...................... 600/160; 600/176; 600/476; 600/478; 359/385; 359/389; 356/317; 356/318; 250/461.2

(58) Field of Classification Search ................ 600/407, 600/473, 476, 160, 176, 182; 359/389, 385, 359/368; 356/317, 318, 337, 341–343; 250/492.22, 250/201.3, 461.2
See application file for complete search history.

(56) References Cited

U.S. PATENT DOCUMENTS

| | | | |
|---|---|---|---|
| 4,634,880 A | | 1/1987 | Lindow et al. |
| 5,028,802 A | * | 7/1991 | Webb et al. ................ 250/235 |
| 5,109,386 A | * | 4/1992 | Bradley ........................ 372/32 |
| 5,120,953 A | | 6/1992 | Harris |
| 5,323,009 A | | 6/1994 | Harris |
| 5,563,710 A | * | 10/1996 | Webb et al. ................ 356/445 |
| 5,742,419 A | | 4/1998 | Dickensheets et al. |
| 5,790,310 A | * | 8/1998 | Huang ........................ 359/618 |
| 5,907,425 A | | 5/1999 | Dickensheets et al. |
| 5,978,095 A | * | 11/1999 | Tanaami ..................... 356/445 |
| 6,007,208 A | | 12/1999 | Dickensheets et al. |
| 6,028,306 A | * | 2/2000 | Hayashi ...................... 250/235 |
| 6,088,145 A | | 7/2000 | Dickensheets et al. |
| 6,154,305 A | | 11/2000 | Dickensheets et al. |
| 6,248,988 B1 | * | 6/2001 | Krantz .................... 250/201.3 |
| 6,252,717 B1 | * | 6/2001 | Grosskopf .................. 359/619 |
| 6,262,423 B1 | * | 7/2001 | Hell et al. ............... 250/458.1 |
| 6,411,835 B1 | * | 6/2002 | Modell et al. .............. 600/407 |
| 6,867,406 B1 | * | 3/2005 | Fairley et al. ........... 250/201.3 |
| 2002/0027708 A1 | * | 3/2002 | Lin et al. .................... 359/385 |
| 2003/0085335 A1 | * | 5/2003 | Almogy et al. .......... 250/208.1 |
| 2005/0078924 A1 | * | 4/2005 | Viellerobe et al. .......... 385/116 |

FOREIGN PATENT DOCUMENTS

JP 2002-277743 9/2002

* cited by examiner

*Primary Examiner*—John P. Leubecker
(74) *Attorney, Agent, or Firm*—Greenblum & Bernstein, P.L.C.

(57) ABSTRACT

An endoscope probe system includes an endoscope probe to be inserted into a body cavity to observe tissue of a living body. The endoscope probe system further includes a laser source that emits multiple laser beams, a light detector having multiple light receiving elements each of which detects intensity of light incident thereon, and a plurality of confocal optical systems arranged to focus the laser beams emitted from the laser source to small spots arranged in a matrix pattern on the target and selectively transmit the laser beams reflected by the target at the spots to respective ones of the light receiving elements of the light detector.

13 Claims, 4 Drawing Sheets

ENDOSCOPE PROBE SYSTEM HAVING CONFOCAL OPTICAL SYSTEMS

BACKGROUND OF THE INVENTION

The present invention relates to an endoscope probe to be inserted into a body cavity to observe in vivo tissues (i.e., tissues of a living body) and an endoscope probe system including such an endoscope probe.

Conventionally, a confocal light scanning probe has been known, which scans a laser beam on tissues within a body cavity through a confocal optical system and receives the laser beam reflected by the tissues through the same confocal optical system to observe a precise surface image or tomogram of the tissues. An example of such a probe is disclosed in Japanese Patent Provisional Publication No. P2002-277743, for example.

Such a confocal light scanning probe selectively receives the laser beam reflected by the tissues at an object side focal plane of an objective lens of the confocal optical system by disposing a pin hole at an image side focal point of the objective lens, which pin hole allows only the light reflected at the object side focal plane to pass therethrough. The reflected light that has passed through the pin hole is then received by a light detector that generates an electrical signal representing the intensity of the reflected light.

To build up a two- or three-dimensional image of the tissues from the output of the light detector, the laser beam emitted from the confocal light scanning probe should be scanned on the target tissues. Therefore, the confocal light scanning probe is generally provided with a scanning mirror for scanning the laser beam on the tissue either two dimensionally or three dimensionally.

The confocal light scanning probe such as one disclosed in the Japanese Patent Application Provisional Publication No. P2002-277743 is provided with a scanning mirror, which is produced by etching a silicon substrate and is typically supported by torsion bars which are produced by etching integrally with the mirror portion. The scanning mirror is generally actuated by an electrostatic force to rotatably vibrate by twisting the torsion bars.

It should be noted that the scanning mirror arranged as above can precisely control the vibrating amplitude of the mirror since it is actuated by a electrostatic force. However, since the required driving voltage of the entire system is quite high, e.g. a few hundreds volts, a leakage current may occur when the confocal light scanning probe is inserted into a body cavity.

Further, the torsion bars supporting the mirror may break when they are twisted by an excessively large force (i.e. when the laser beam scanning range is too large), or for a large number of times (i.e. when the laser beam scanning is carried out for a long time).

Further, the conventional confocal light scanning probe requires a finite duration of time for scanning an area on the tissue to be observed using a beam. Therefore, it is difficult to achieve real time observation of the tissue by using the confocal light scanning probe.

SUMMARY OF THE INVENTION

The present invention is advantageous in that an endoscope probe that overcomes the above mentioned problems of conventional confocal light scanning probes utilizing a scanning mirror is provided.

According to an aspect of the invention an endoscope probe system including an endoscope probe to be inserted into a body cavity to observe tissue of a living body is provided. The endoscope probe system has a laser source that emits multiple laser beams, a light detector having multiple light receiving elements each of which detects intensity of light incident thereon, and a plurality of confocal optical systems arranged to focus the laser beams emitted from the laser source to small spots on the target and selectively transmit the laser beams reflected by the target at the spots to respective ones of the light receiving elements of the light detector.

In the endoscope probe system arranged as above, multiple laser beams can be simultaneously irradiated on the target, and the intensity of the laser beams reflected by the target tissue at multiple spots on the target can be simultaneously detected by the light detector without scanning a laser beam, or without providing a scanning mirror to the endoscope probe for scanning a laser beam.

Optionally, the plurality of confocal optical systems may focus the laser beams emitted from the laser source to small spots arranged in a regular pattern such as a matrix pattern.

In some embodiments of the invention, the plurality of confocal optical systems have a common objective lens system, which may be a reducing lens system, and a common light shielding member disposed between the objective system and the light detector. The objective lens focuses the laser beams emitted from the laser source to the small spots on the target. The light shielding member has a plurality of minute transparent portions, which may be pin holes, located at positions conjugate to the spots to which the laser beams are focused by the objective lens system. The light detector receives the laser beams reflected by the target through the minute transparent portions of the light shielding member.

The plurality of confocal optical systems may further include a common beam splitter cube that supports the laser source, the light detector and the light shielding member. The beam splitter cube may direct the laser beams emitted from the laser source to the objective lens system while transmitting light reflected back from the target and passed through the light shielding member to the light detector.

In addition to the above, a first lens array may be interposed between the light shielding member and the beam splitter cube to collimate the laser beam reflected back by the target and passed through the minute transparent portions of the light shielding member, and a second lens array may be interposed between the light detector and the beam splitter cube to converge the laser beams traveling from the light shielding member toward the light detector on the light receiving elements of the light detector.

Further, a third lens array may be interposed between the laser source and the beam splitter cube to collimate the laser beams emitted from the laser source.

Each of the first, second, and third lens arrays may be formed on one side of a glass plate by locally changing the refractive index of said glass plate.

The laser source, the light detector, and the light shielding member may be arranged within the endoscope probe.

In some other cases of the invention, the plurality of confocal optical systems includes a common objective lens system, which may be a reducing lens system, and a plurality of optical fibers disposed between the objective lens and the light detector with distal end surfaces of the optical fibers disposed to face the objective lens system. The objective lens focuses the laser beams emitted. from the laser source to the small spots on the target. The distal end surfaces of the optical fibers are disposed at positions conjugate to the spots to which the laser beams are focused by the objective lens.

The light detector receives the laser beams reflected by the target through the optical fibers.

In the case above, the plurality of confocal optical system may also include a common beam splitter cube that supports the laser source and the light detector, which beam splitter cube directs the laser beams emitted from the laser source to the objective lens system while transmitting light reflected back from the target and passed through the optical fibers to the light detector.

Further, a first lens array may be interposed between the optical fibers and the beam splitter cube to collimate the laser beams reflected back by the target and passed through the optical fibers, and a second lens array may be interposed between the light detector and the beam splitter cube to converge the laser beams emitted from the optical fibers and traveling toward the light detector on the light receiving elements of the light detector.

In addition to the above, a third lens array may be interposed between the laser source and the beam splitter cube to collimate the laser beams emitted from the laser source.

The laser source, the light detector, and the beam splitter cube supporting the laser source and the light detector may be placed outside the endoscope probe. In this case, proximal end surfaces of the optical fibers are disposed in a vicinity of the beam splitter cube to receive the laser beams emitted from the laser source through the beam splitter cube and emit the laser beams reflected back by the target toward the light detector through the beam splitter.

BRIEF DESCRIPTION OF THE ACCOMPANYING DRAWINGS

FIG. 1 schematically illustrates a configuration of an endoscope probe system according to a first embodiment of the invention;

FIG. 2 schematically shows a side view of an objective lens system and an beam splitter unit of the endoscope probe system shown in FIG. 1;

DETAILED DESCRIPTION OF THE EMBODIMENTS

Hereinafter, embodiments of the present invention will be described with reference to the accompanying drawings.

Figure 1:
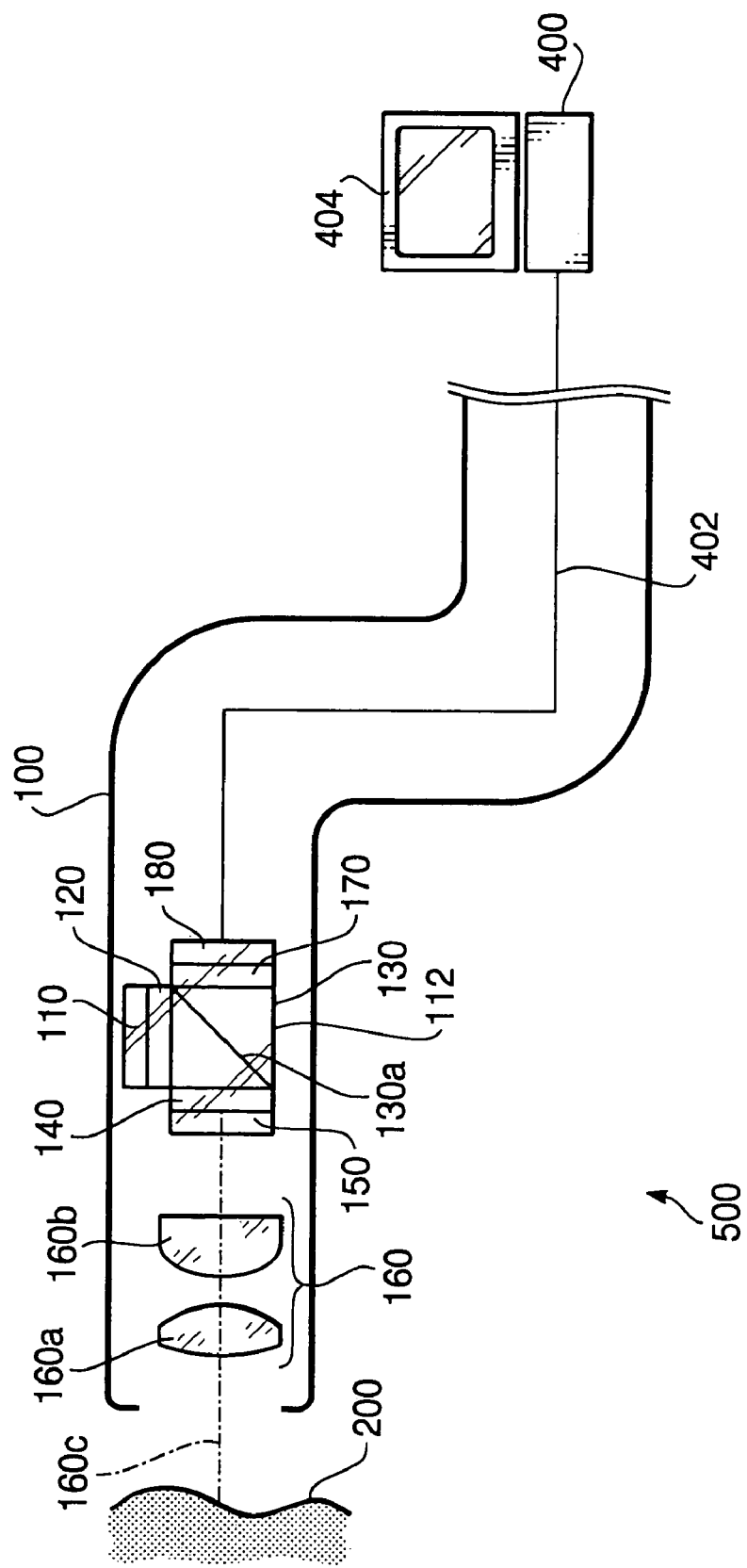

FIG. 1 schematically illustrates a configuration of an endoscope probe system 500 according to a first embodiment of the invention. The endoscope probe system 500 includes an endoscope probe 100 and a personal computer 400 electrically connected with the endoscope probe 100. The endoscope probe 100 has an elongated shape that can be inserted into a human body cavity through an accessory channel of an endoscope. The endoscope probe 100 inserted into the body cavity irradiates multiple laser beams on target tissues and detects the intensities of the laser beams reflected by the target tissue. The personal computer 400 receives electrical signals corresponding to the detected light intensities received from the endoscope probe 100 and generates a surface image or a tomogram of the target tissues using an image processing program which may be pre-installed in the personal computer 400.

Hereinafter, a configuration of the endoscope probe system 500 and an operation of an optical system thereof will be described.

The endoscope probe 100 includes a surface emitting laser array 110, an objective lens system 160, a CCD (charge coupled system) 180, and a beam splitter unit 112. The beam splitter unit 112 includes a micro collimating lens array plate 120, a beam splitter cube 130, a first micro focusing lens array plate 140, an aperture plate 150, and a second micro focusing lens array plate 170.

Figure 2:
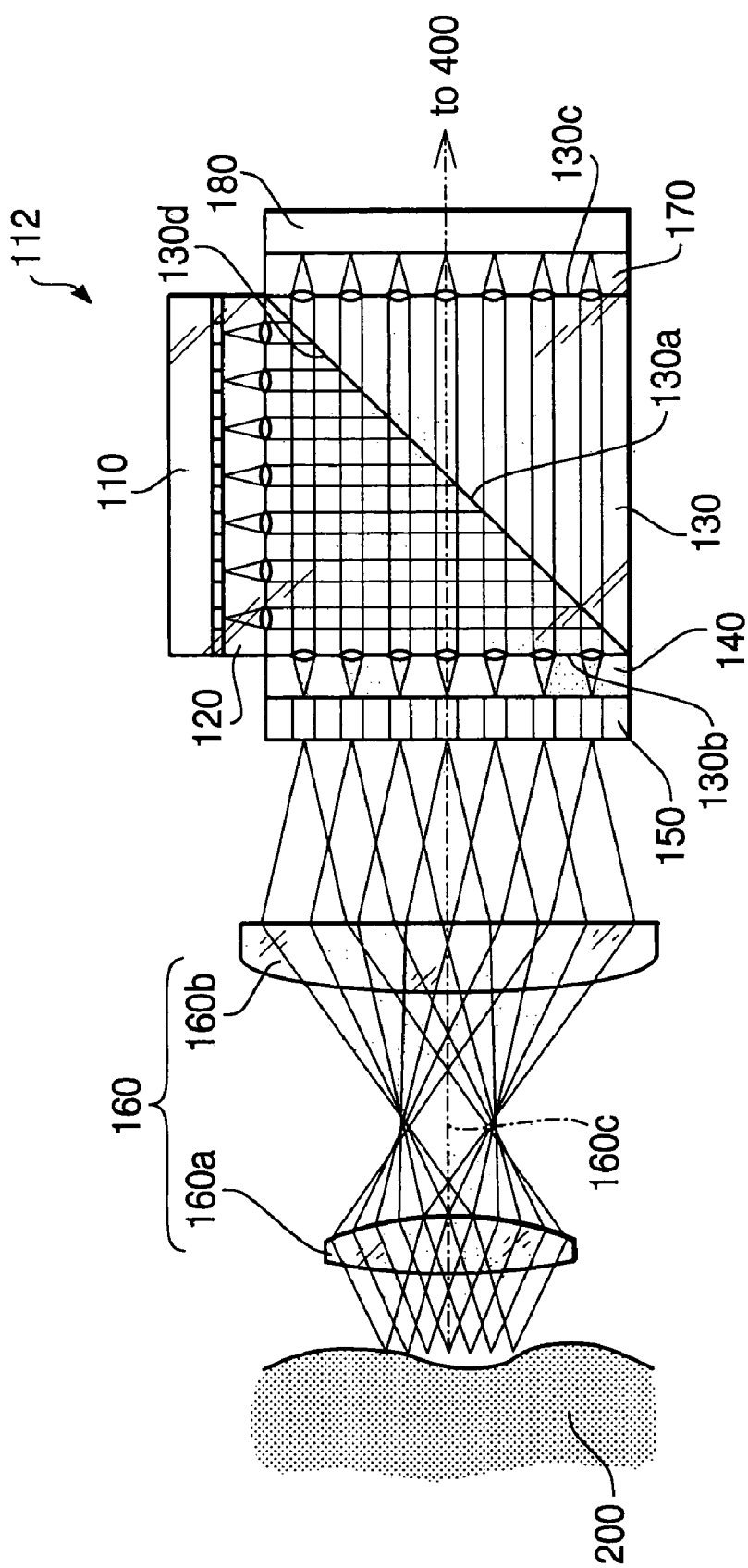

FIG. 2 schematically shows a side view of the objective lens system 160 and the beam splitter unit 112 shown in FIG. 1. The beam splitter cube 130 is arranged such that a distal end surface 130b and a proximal end surface 130c thereof are perpendicular to an optical axis 160c of the objective lens system 160. The first micro focusing lens array plate 140 and the aperture plate 150 are fixed in this order on the distal end surface 130b, which faces the objective lens system 160, by means of adhesive. The second micro focusing lens array plate 170 and the CCD 180 are fixed in this order on the proximal end surface 130c by means of adhesive. Further, the micro collimating lens array plate 120 and the surface emitting laser array 110 are provided on a top face 130d of the beam splitter cube 130 in this order by means of adhesive.

The surface emitting laser array 110 is an array of multiple semiconductor lasers formed on a common semiconductor substrate such that the laser cavity of each laser is vertical to the common semiconductor substrate. The laser cavities are arranged in a matrix pattern so that multiple laser beams are emitted from positions corresponding to the positions of the light receiving elements of the CCD 180. Each laser cavity has a size of a few am. The surface emitting laser is advantageous in that the threshold current thereof for emitting a laser beam is quite low and the current consumption is also quite small, i.e., less than 1 mA. In the present embodiment, the surface emitting laser array 110 is disposed so that multiple laser beams are emitted therefrom toward the micro collimating lens array plate 120.

Figure 3:
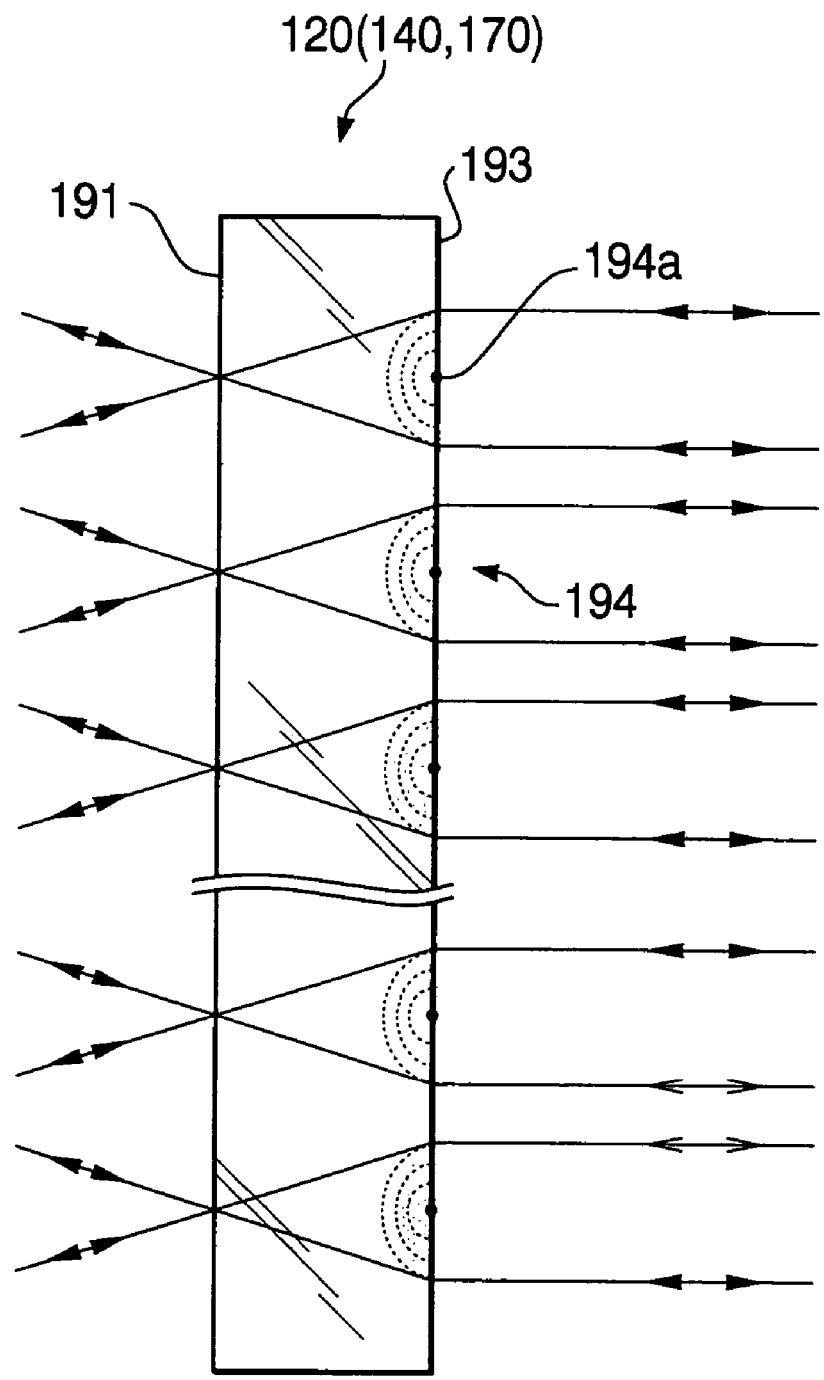
FIG. 3 is a sectional view of an micro lens array.

FIG. 3 is a sectional view of an optical element that is utilized in the present embodiment as the micro collimating lens array plate 120, the first micro focusing lens array plate 140, and the second micro focusing lens array plate 170. The optical element shown in FIG. 3 is a glass plate having a first surface 191 and a second surface 193. Both first and second surfaces 191 and 193 are plane and parallel to each other. A plurality of micro lenses 194 are formed on the second surface 193 in a matrix pattern. Each micro lens 194 is configured such that the refractive index of the glass gradually changes (e.g., decreases) in accordance with a distance from a center 194a of the micro lens 194. Each micro lens 194 is formed so that a parallel light beam entering the micro lens 194 from the second surface 193 is converged in a vicinity of the first surface 191 before emerging from the lens array plate 120.

The number of the micro lenses 194 formed on the lens array plate 120 is the same as the number of the laser cavities formed on the surface emitting laser array 110 (or the number of the laser beams emitted from the surface emitting laser array 110). Further, the micro lenses 194 are formed at positions corresponding to the positions of the laser cavities. In other words, the micro lenses 194 are arranged such that the centers 194a thereof can be placed on the optical paths of the primary rays of the laser beams emitted from the surface emitting laser array 110.

Referring back to FIG. 2, the micro collimating lens array plate 120, or the glass plate shown in FIG. 3, is disposed between the surface emitting laser array 110 and the beam splitter cube 130 so that the laser beams emitted by the surface emitting laser array 110 enter the micro collimating lens array plate 120 through the first surface 191 and emerge from the second surface 193.

The first micro focusing lens array plate 140, which has the same configuration as the lens array plate 120 shown in FIG. 3, is attached on the distal end surface 130b of the beam splitter cube 130 so that the second surface 193 of the first micro focusing lens array plate 140 faces the beam splitter cube 130 and the first surface 191 faces the aperture plate 150.

Further, the second micro focusing lens array plate 170, which also has the same configuration as the glass plate shown in FIG. 3, is attached on the proximal end surface 130c of the beam splitter cube 130 with the second surface 193 facing the beam splitter cube 130 and the first surface 191 facing the CCD 180.

The laser beams emitted from the surface emitting laser array 110 enter the micro collimating lens array plate 120 through the first surface 191, collimated by the micro lenses 194, and emerge from the second surface 193.

Then, the collimated laser beams enter the beam splitter cube 130. The beam splitter cube 130 bends the optical paths of the laser beams at an angle of 90 degrees by a half mirror 130a thereof so that the laser beams travel toward the objective lens system 160.

Next, the laser beams emerge from the beam splitter cube 130 through the distal end surface 130b thereof and enter the first micro focusing lens array plate 140 through the second surface 193 thereof. The laser beams are converged by the micro lenses 194 of the first micro focusing lens array plate 140 on or near the first surface 191 and then emerge from the first micro focusing lens array plate 140.

Next, the laser beams emitted from the first micro focusing lens array plate 140 pass through the aperture plate 150. The aperture plate 150 is a light shielding member taking the form of a sheet and provided with multiple pin holes arranged in a matrix pattern. The number of the pin holes of the aperture plate 150 is the same as the number of the micro lenses 194 formed on the first focusing micro lens array plate 140, and the pin holes are formed at positions corresponding to the micro lenses 194. The aperture plate 150 is attached on the first surface 191 of the first micro focusing lens array plate 140.

The laser beams emerging from the first micro focusing lens array plate 140 passes through respective ones of the pin holes of the aperture plate 150 and enter the objective lens system 160.

The objective lens system 160 is a telecentric optical system including a focusing lens 160a and a collimating lens 160b. The objective lens system 160 is arranged as a reducing lens system. Thus, the focal distance thereof is short and the numerical aperture (NA) thereof is large. With this objective lens system 160, a small area of a target tissue 200 can be observed in high resolution.

The objective lens system 160 focuses the laser beams to small spots at the focal plane thereof, which focal plane is located on or slightly below the surface of the target tissue 200. The laser beams striking the tissue are partially reflected back by the tissue, pass through the objective lens system 160 and impinge on the aperture plate 150.

In the present embodiment, the aperture plate 150 is disposed such that the pin holes thereof are located at positions conjugate to the spots to which the objective lens system 160 focuses the laser beams. Thus, the laser beams reflected back from the above-mentioned spots is collected by the objective lens system 160 and converged on the pin holes. The pin holes allows the light reflected back at the above-mentioned spots to pass therethrough but reject the light that does not originate from those spots.

The beams of the reflected light that have passed through the pin holes of the aperture plate 150 enter the first micro focusing lens array plate 140 to be collimated thereby. Then, the beams of the reflected light enter the beam splitter cube 130, pass through the half mirror 130a, and emerge from the proximal end surface 130c of the beam splitter cube 130. Then, the beams of the reflected light pass through the second micro focusing lens array plate 170 to be converged onto the CCD 180 so that the beams of the reflected light impinge on respective ones of the light receiving elements of the CCD 180. Then, the CCD 180 converts each beam of the reflected light into a electrical signal representing the light intensity of the reflected light and then outputs the electrical signals, or image signals, to the personal computer 400.

As shown in FIG. 1, the personal computer 400 is connected with the endoscope probe 100, or the CCD 180, by a communication cable 402. The personal computer 400 is provided with an image processing program for processing the image signals received from the endoscope probe 100 into an image that can be displayed on a monitor. The image signals transmitted from the endoscope probe 100 is processed by this image processing program and the image obtained thereby is displayed on a monitor 404 connected to the personal computer 400.

As described above, in the endoscope probe 100 arranged as above, the objective lens system 160 and the beam splitter unit 112 defines multiple confocal optical systems which allows the CCD 180 to simultaneously detect the intensities of the laser beams reflected by the target tissue at multiple spots arranged in a matrix pattern on or slightly below the surface of the target tissue 200. Thus, a two dimensional image of the surface or a layer defined slightly below the surface of the target tissue 200 can be obtained without scanning a laser beam on the tissue.

Further, in the endoscope probe 100 arranged as above, the laser beams reflected by the target tissue 200 are converged by the second micro focusing lens array plate 170 on respective ones of the light receiving elements of the CCD 180 and do not strike areas out of the light receiving elements. Thus, the CCD 180 can effectively receive the reflected lights.

It should be noted that when the pin holes on the aperture plate 150, and the micro lenses 194 on the first and second micro focusing lens array plates 140 and 170 are arranged at the same interval as that of the light receiving elements of the CCD 180, the beams of reflected light impinge perpendicularly onto respective light receiving elements and allow the light receiving elements to receive the light effectively.

It should be noted that since the surface emitting laser array 110 is provided in the endoscope probe 100, it is not necessary to prepare an external light source for observing living tissue inside the body cavity by the endoscope probe 100. Further, since the surface emitting laser array 110 emits laser beams at lower power consumption voltages compared to the laser source conventionally used for endoscope probes, the endoscope probe 100 according to the present embodiment can be operated by low energy.

Hereinafter, a second embodiment of the invention will be described with reference to FIG. 4., in which elements that are substantially the same as those described in the first embodiment are denoted by the same reference numbers.

Figure 4:
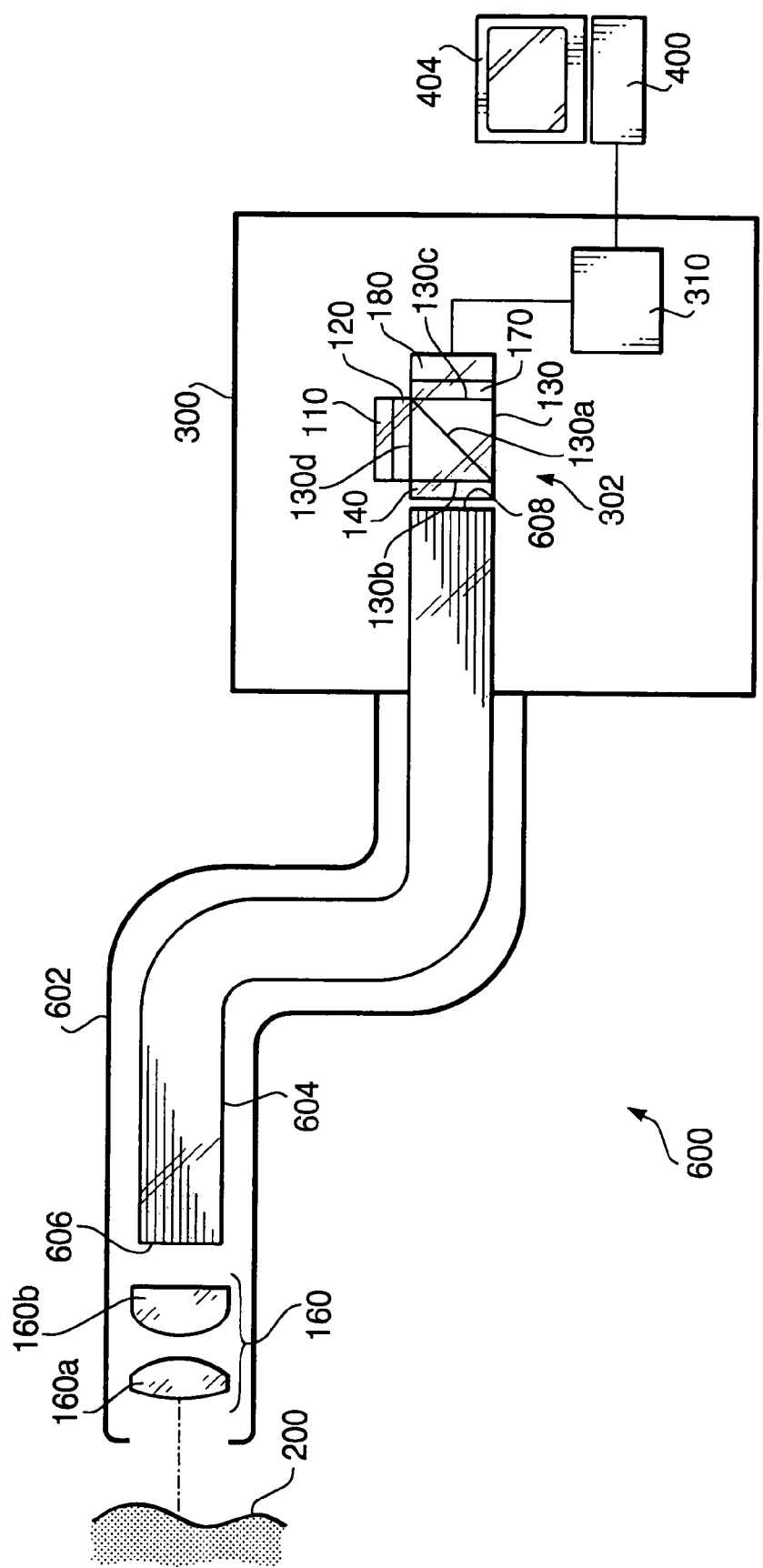
FIG. 4 shows a configuration of an endoscope probe system according to an second embodiment of the invention.

FIG. 4 shows a configuration of an endoscope probe system 600 according to the second embodiment of the invention. The endoscope probe system 600 includes an endoscope probe 602, a processor 300, and the personal computer (PC) 400.

As with the endoscope probe 100 shown in FIG. 1, the endoscope probe 602 according to second embodiment of the invention is provided with the objective optical lens system 160. The endoscope probe 602 is further provided with an optical fiber bundle 604 which optically connects the objective lens system 160 with the processor 300.

The processor 300 is provided with the surface emitting laser array 110, the CCD 180, a beam splitter unit 302, and an image processing circuitry 310.

The beam splitter unit 302 of the present embodiment has the same configuration as the beam splitter unit 112 shown in FIG. 2 except that it is not provided with the aperture plate 150. That is, the beam splitter unit 302 is composed of the beam splitter cube 130, the micro collimating lens array plate 120, the first micro focusing lens array plate 140, and the second micro focusing lens array plate 170. As with the first embodiment of the invention, the first micro focusing lens array plate 140 is fixed on the distal end surface 130b of the beam splitter cube 130. The second micro focusing lens array plate 170 and the CCD 180 are fixed in this order on the proximal end surface 130c, and the micro collimating lens array plate 120 and the surface emitting laser array 110 are fixed in this order on the top face 130d of the beam splitter cube 130.

The optical fiber bundle 604 extends through the endoscope probe 602 so that a distal end surface 606 of the optical fiber bundle 604 faces the objective lens system 160. A proximal end portion of the optical fiber bundle 604 is connected to the processor 300 so that a proximal end surface 608 of the optical fiber bundle 604 faces the first micro focusing lens array plate 140.

The optical fiber bundle 604 includes a plurality of single mode optical fibers. The single mode optical fibers are tied in a bundle so that the proximal end surfaces thereof are arranged in a matrix pattern corresponding to the arrangement of the micro lenses 194 (as shown in FIG. 3) of the first micro focusing lens array plate 140.

In the endoscope probe system 600 arranged as above, the laser beams emitted from the surface emitting laser array 110 are collimated by the micro collimating lens array 120, and bent by the half mirror 130a of the beam splitter cube 130 at an angle of 90 degrees. Then, the laser beams enter the first micro focusing lens array plate 140 to be converged in a vicinity of the first surface 191 (as shown in FIG. 3).

The proximal end surface 608 of the optical fiber bundle 604 is located in a vicinity of the first micro focusing lens array plate 140 to receive the laser beams converged by the first micro focusing lens array plate 140. Thus, the laser beams are transmitted by the optical fiber bundle 604 to the objective lens system 160.

Next, the laser beams are irradiated on the target tissue 200 through the objective lens system 160. As with the first embodiment of the invention, the objective lens system 160 focuses the laser beams to small spots at the focal plane thereof on or slightly below the surface of the target tissue 200.

The laser beams irradiated on the target tissue 200 are partially reflected back by the target tissue 200 toward the optical fiber bundle 604.

The distal end surface 606 of the optical fiber bundle 604 is disposed such that the end surface of each single mode optical fiber is located at a position conjugate to the spot to which the objective lens system 160 focuses the laser beam emitted from the same optical fiber. Thus, the light reflected back from the above-mentioned spots is collected by the objective lens system 160 and converged on respective end surfaces of the optical fibers. Since the diameter of the core of the single mode optical fiber is quite small, the end surface of each optical fiber serves as a pin hole. That is, the optical fibers allow the laser beams reflected back at the above-mentioned spots to enter the optical fibers but reject the lights that does not originate from those spots.

The reflected laser beams that have entered the optical fiber bundle 604 travel therethrough and emerge from the proximal end of the optical fiber bundle 604. Then, the reflected laser beams emitted from the optical fiber bundle 604 transmit through the first micro focusing lens array plate 140 and the beam splitter cube 130. Within the beam splitter cube 130, the reflected laser beams pass through the half mirror 130a. Then, the reflected laser beams enter the second micro focusing lens array plate 170 which converges the laser beams on the CCD 180. The CCD 180 converts the laser beams into electric signals to generate image signals and sends the image signals to the image processing circuitry 310. The image processing circuitry 310 processes the image signals to produce an observation image which is displayed on the monitor 404 through the personal computer 400.

As described above, in the endoscope probe 100 arranged as above, the objective lens system 160, the optical fiber bundle 604, and the beam splitter unit 302 define multiple confocal optical systems. The multiple confocal optical systems focus the laser beams emitted by the surface emitting laser array 110 to the small spots on the target tissue 200. Further, the multiple confocal optical systems receive and transmit the laser beams reflected by the target tissues at the above mentioned spots to the CCD 180 so that the CCD 180 can generate signals representing the intensities of the reflected laser beams. The signals generated by the CCD 180 in a manner as described above allows generation of a surface image or tomogram of the target tissue 200 although the laser beams are not scanned on the target tissue 200.

Note that, in the endoscope probe system 600 according to the second embodiment of the invention, the beam splitter unit 302, the surface emitting laser array 110, and the CCD 180 are located in the processor 300, and the endoscope probe 602 is provided only with the objective lens system 160 and the optical fiber bundle 604. Therefore, the configuration of the endoscope probe 602 is simple, and hence the endoscope probe 602 can be produced in a light weight and in a small diameter to improve the operability thereof.

While the invention has been described in detail with reference to specific embodiments thereof, it would be apparent to those skilled in the art that various changes and modifications may be made therein without departing from the spirit of the invention.

For example, the aperture plate 150 of the endoscope probe 100 shown in FIG. 1 can be replaced with a coating applied on the first micro focusing lens array plate 140, which coating is provided with multiple minute holes formed at positions corresponding to the micro lenses of the first micro focusing lens array plate 140. The coating may be made of any material that is capable of cutting off light. An example of such a coating is a thin metal layer formed by vapor deposition. The replacement of the aperture plate 150 with the above-mentioned coating allows reduction of a component count of the endoscope probe as well as downsizing of the endoscope probe.

The endoscope probe 100 and the personal computer 400 of the first embodiment of the invention may be provided with systems for transmitting the image signals therebetween by wireless communication so that the endoscope probe system 600 can be configured without the communication wire 402 extending between the endoscope probe 100 and the personal computer 400. In this case, the endoscope probe 100 may be provided with a battery for supplying power to the surface emitting laser array 110. It should be noted that, since the power required by the surface emitting laser array 110 for emitting the laser beams is much lower than other laser sources conventionally utilized for similar endoscope probes, the battery to be provided to the endoscope probe 100 can be a light and small one. Therefore, a compact portable endoscope probe having a wireless communication function can be provided by modifying the first embodiment of invention.

The present disclosure relates to the subject matter contained in Japanese Patent Application No. P2003-12787, filed on Jan. 21, 2003, which is expressly incorporated herein by reference in its entirety.

What is claimed is:

1. An endoscope probe system including an endoscope probe to be inserted into a body cavity to observe in vivo tissues, comprising:

a laser source that emits a plurality of laser beams;

a light detector having a plurality of light receiving elements, each of said light receiving elements detecting intensity of light incident thereon; and a plurality of confocal optical systems arranged to converge the plurality of laser beams emitted by said laser source to small spots on the tissues and selectively transmit the plurality of laser beams reflected by the tissues to said light receiving elements of said light detector, respectively, wherein said plurality of confocal optical systems have a common objective lens system and a common light shielding member disposed between said objective lens system and said light detector, wherein said objective lens system converges the laser beams emitted from said laser source to the small spots on the tissues, wherein said light shielding member has a plurality of minute transparent portions located at positions conjugate to the spots to which the laser beams are focused by said objective lens system, wherein said light detector receives the laser beams reflected by the tissues through said minute transparent portions of said light shielding member, wherein said minute transparent portions are pin holes formed on said light shielding member, wherein said plurality of confocal optical systems includes a common beam splitter cube that supports said laser source, said light detector and said light shielding member directing the laser beams emitted by said laser source to said objective lens system while transmitting light reflected back from the tissues and passed through said light shielding member to said light detector, wherein a first lens array is interposed between said light shielding member and said beam splitter cube to collimate the laser beam reflected back by the target and passed through said minute transparent portions of said light shielding member, and wherein a second lens array is interposed between said light detector and said beam splitter cube to converge the laser beams traveling from said light shielding member toward said light detector on said light receiving elements of said light detector.

2. The endoscope probe system according to claim 1, wherein said plurality of confocal optical systems are arranged such that the plurality of laser beams emitted by said laser source are converged at positions, on the tissues, in a regular pattern.

3. The endoscope probe system according to claim 2, wherein the regular pattern is a matrix pattern.

4. The endoscope probe system according to claim 1, wherein said objective lens system is a reducing lens system.

5. The endoscope probe system according to claim 1, wherein a third lens array is interposed between said laser source and said beam splitter cube to collimate the laser beams emitted from said laser source.

6. The endoscope probe system according to claim 5, wherein each of said first, second, and third lens arrays is formed on one side of a glass plate by locally changing the refractive index of said glass plate.

7. The endoscope probe system according to claim 1, wherein said laser source, said light detector, and said light shielding member are arranged within said endoscope probe.

8. The endoscope probe system according to claim 1, wherein said laser source is a surface emitting laser.

9. An endoscope probe system including an endoscope probe to be inserted into a body cavity to observe in vivo tissues, comprising:

a laser source that emits a plurality of laser beams;

a light detector having a plurality of light receiving elements, each of said light receiving elements detecting intensity of light incident thereon; and a plurality of confocal optical systems arranged to converge the plurality of laser beams emitted by said laser source to small spots on the tissues and selectively transmit the plurality of laser beams reflected by the tissues to said light receiving elements of said light detector, respectively, wherein said plurality of confocal optical systems includes a common objective lens system and a plurality of optical fibers disposed between said objective lens and said light detector with distal end surfaces of said optical fibers disposed to face said objective lens system, wherein said objective lens focuses the laser beams emitted from said laser source to the small spots on the target, wherein said distal end surfaces of said optical fibers are disposed at positions conjugate to the spots to which the laser beams are focused by said objective lens, wherein said light detector receives the laser beams reflected by the target through said optical fibers, wherein said plurality of confocal optical systems include a common beam splitter cube that supports said laser source and said light detector and directs the laser beams emitted from said laser source to said objective lens system while transmitting light reflected back from the target and passed through said optical fibers to said light detector, wherein a first lens array is interposed between said optical fibers and said beam splitter cube to collimate the laser beams reflected back by the target and passed through said optical fibers, and wherein a second lens array is interposed between said light detector and said beam splitter cube to converge the laser beams emitted from said optical fibers and traveling toward said light detector on said light receiving elements of said light detector.

10. The endoscope probe system according to claim 9, wherein said objective lens system is a reducing lens system.

11. The endoscope probe system according to claim 9, wherein a third lens array is interposed between said laser source and said beam splitter cube to collimate the laser beams emitted from said laser source.

12. The endoscope probe system according to claim 11, wherein each of said first, second, and third lens arrays is formed on one side of a glass plate by locally changing the refractive index of said glass plate.

13. The endoscope probe system according to claim 9, wherein said laser source, said light detector, and said beam splitter cube supporting said laser source and said light detector are placed outside said endoscope probe, and wherein proximal end surfaces of said optical fibers are disposed in a vicinity of said beam splitter cube to receive the laser beams emitted from said laser source through said beam splitter cube and emit the laser beams reflected back by the target toward said light detector through said beam splitter.

\* \* \* \* \*